United States Patent [19]

Choi et al.

[11] Patent Number: 5,405,965

[45] Date of Patent: Apr. 11, 1995

[54] PROCESSES FOR PREPARATION OF 5-PYRAZOLEMERCAPTAN DERIVATIVES AND INTERMEDIATES THEREOF

[75] Inventors: Jong K. Choi; In B. Jhung; Jae C. Lee; Jong S. Sa; Sung J. Jo; Jin H. Cho, all of Daejeon, Rep. of Korea

[73] Assignee: Lucky Ltd., Seoul, Rep. of Korea

[21] Appl. No.: 166,864

[22] Filed: Dec. 15, 1993

[30] Foreign Application Priority Data

Dec. 17, 1992 [KR] Rep. of Korea .................. 92-24734
Dec. 17, 1992 [KR] Rep. of Korea .................. 92-24736
Dec. 22, 1992 [KR] Rep. of Korea .................. 92-25112
Mar. 9, 1993 [KR] Rep. of Korea .................. 93-3512

[51] Int. Cl.$^6$ .................................... C07D 231/18
[52] U.S. Cl. ........................................ 548/369.7
[58] Field of Search ............................ 548/364.7

[56] References Cited

U.S. PATENT DOCUMENTS 4,064,262 12/1977 Serban et al. .
4,954,164 9/1990 Suzuki et al. .

OTHER PUBLICATIONS

K. A. Jensen et al., ACTA Chemica Scandinavica 23, vol. 6, pp. 1916-1934 (1969).

Primary Examiner—Robert W. Ramsuer
Attorney, Agent, or Firm—Willian Brinks Olds Hofer Gilson & Lione

[57] ABSTRACT

The present invention relates to a process for preparation of 5-pyrazolemercaptan derivatives represented by the following general formula (I), which is useful for synthesis of sulfonyl-urea-based herbicides, and an intermediate thereof,

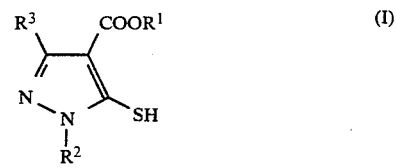

wherein
 $R^1$ represents hydrogen, $C_1$-$C_4$ alkyl, allyl or propargyl,
 $R^2$ represents hydrogen, $C_1$-$C_4$ alkyl, or a phenyl group which can contain one or more substituent selected from the group consisting of halogen, nitro and methyl at an optional position, and
 $R^3$ represents hydrogen, methyl, ethyl or phenyl.

4 Claims, No Drawings

PROCESSES FOR PREPARATION OF 5-PYRAZOLEMERCAPTAN DERIVATIVES AND INTERMEDIATES THEREOF

BACKGROUND OF THE INVENTION

1. Field of the Invention

The present invention relates to a process for preparation of 5-pyrazolemercaptan derivatives useful for synthesis of sulfonylurea-based herbicides. More particularly, the present invention relates to a process for preparation of 5-pyrazolemercaptan derivatives represented by the following general formula (I):

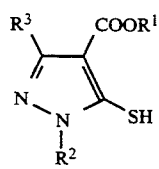

wherein $R^1$ represents hydrogen, $C_1$–$C_4$ alkyl, allyl or propargyl, $R^2$ represents hydrogen, $C_1$–$C_4$ alkyl, or a phenyl group which can contain one or more substituent selected from the group consisting of halogen, nitro and methyl at an optional position, and $R^3$ represents hydrogen, methyl, ethyl or phenyl. Further, the present invention also relates to a process for preparation of an intermediate used in the preparation of the compound of formula (I) above.

2. Background art

The compounds, of formula (I), as defined above, are the known compound of which the method for preparation has been described in, for example, European Laid-open Patent Publication No. 87,780, Japanese Laid-open Patent Publication No. (sho) 61-210,003, Japanese Laid-open Patent Publication No. (sho) 61-210,084, etc. Specifically, Japanese Laid-open Patent Publication No. (sho) 61-210,084 describes a method for preparation of the compound (I') comprising the procedure of three steps starting from diethylethoxy methylene malonate according to the following reaction scheme:

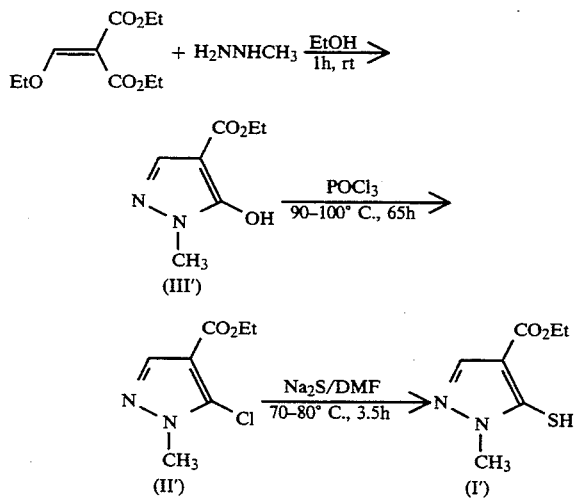

According to the above method, in detail, diethylethoxy methylene malonate is initially cyclized with methyl hydrazine to produce the compound of the above formula (III'), a hydroxy group of the compound (III') is subsequently replaced with a chlorine atom by reacting the compound (III') with phosphorus oxychloride ($POCl_3$) at the temperature of 90° to 100° C. for 65 hours or more and then the resulting compound (II') is reacted with sodium sulfide ($Na_2S$) in the presence of dimethylformamide (DMF) solvent at the temperature of 70° to 80° C. for 3.5 hours to prepare the final compound of formula (I').

However, the prior known method as described above has some disadvantages in that the desired compound is prepared through a complex reaction procedure comprising three reaction steps, the product from the first cyclization step may contain a regioisomeric compound of the following formula (I'') as by-product to reduce the purity of the product and therefore should be further subjected to a purification procedure, such as recrystallization, and the whole reaction procedure requires a high reaction temperature and a long reaction time and provides the yield as low as 80% and less (particularly, the yield in the chlorination step is merely 30 to 40%):

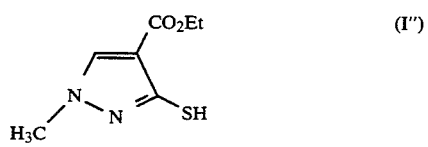

Thus, the present inventors have continuously studied to develop a method which can more efficiently and economically prepare the compound of the above formula (I). As a result, we have found that the compound of formula (I) can be efficiently prepared starting from a certain ethylidene dithiocarbazic acid derivative in one step procedure and then completed the present invention.

Therefore, it is an object of the present invention to provide a novel and improved process for preparation of 5-pyrazolemercaptan derivatives having the general formula (I), as defined above.

It is further object of the present invention to provide a novel intermediate to be used in the process for preparation of the compound of formula (I).

Further, it is another object of the present invention to provide a novel process for preparation of some intermediates used for preparing the compound of formula (I).

The more pertinent and important features of the present invention have been outlined above in order that the detailed description of the invention which follows will be better understood and that the present contribution to the art can be fully appreciated. Those skilled in the art can appreciate that the conception and the specific embodiment disclosed herein may be readily utilized as a bases for modifying or designing other structures for carrying out the same purposes of the present invention. Further, those skilled in the art can realize that such equivalent constructions do not depart from the spirit and scope of the invention as set forth in the claims.

DISCLOSURE OF INVENTION

In one aspect, the purpose of the present invention is to provide a process for preparation of 5-pyrazolemercaptan derivatives represented by the following general formula (I),

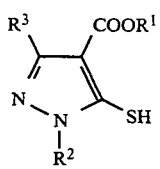

wherein $R^1$ represents hydrogen, $C_1$-$C_4$ alkyl, allyl or propargyl, $R^2$ represents hydrogen, $C_1$-$C_4$ alkyl, or a phenyl group which can contain one or more substituent selected from the group consisting of halogen, nitro and methyl at an optional position, and $R^3$ represents hydrogen, methyl, ethyl or phenyl, characterized in that a malonate compound of the following formula (III),

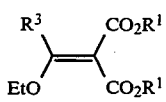

wherein $R^1$ and $R^3$ are defined as above, is reacted with a dithiocarbazate compound of the following formula (II),

wherein R represents $C_1$-$C_4$ alkyl (preferably, methyl or ethyl), $C_2$-$C_4$ alkenyl (preferably, allyl), aralkyl (preferably, benzyl) or aryl (preferably, phenyl) and $R^2$ is defined as above, in the presence of a base.

The process according to the present invention as described above can be represented by the following reaction scheme (1).

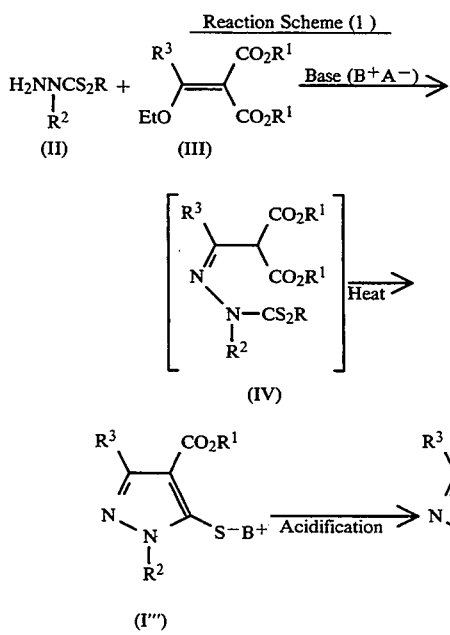

In the above reaction scheme, R, $R^1$, $R^2$ and $R^3$ are defined as above, $B^+$ represents a base radical and $A^-$ represents an acid radical. According to the reaction scheme (1), first the compound of formula (II) is reacted with the compound of formula (III) to produce an ethylidene dithiocarbazate compound of formula (IV) and the resulting compound of formula (IV) is directly decarboxylated to form a cycle to produce a pyrazole-mercaptan basic salt of formula (I''') which is then subjected to acidification to prepare the desired pyrazole-mercaptan compound of formula (I).

Preferably, the above reaction can be practiced in the nitrogen atmosphere under an anhydrous condition to provide a good result.

Although the reaction of the present invention is conducted substantially in a stoichiometric manner, if required, the compound of formula (III) can be generally used in a larger amount, preferably in the ratio of 1.0 to 2.0 equivalent weight and particularly of 1.0 to 1.1 equivalent weight, with respect to the compound of formula (II).

The reaction according to the present invention can be carried out in the absence of a solvent. However, the reaction is preferably carried out in the presence of a solvent and is completed within 8 to 20 hours. For this purpose, any solvent which has no adverse effect on the reaction, for example, alcohols such as methanol, ethanol, t-butanol, etc., alkyl halides such as ethylene dichloride, methylene dichloride, etc., or benzene, n-hexane, toluene and the like, can be used, with alcohols, particularly ethanol being preferable. Although the reaction temperature can be in the range of 0° C. to 150° C., the reaction is preferably carried out at the refluxing temperature of the solvent to be used in this reaction.

The base which can be preferably used in the reaction according to the present invention includes ($C_1$-$C_5$) alkoxides, hydroxides or carbonates of alkali metal such as sodium, potassium, lithium, etc. or tertiary amine bases such as pyridine, triethylamine, etc., with alkali metal ($C_1$-$C_5$) alkoxide or alkali metal hydroxide, particularly sodium ethoxide or sodium hydroxide, being most preferable. The base is used in an amount of 1.0 to 5.0 equivalent weight, preferably 1.1 to 1.5 equivalent weight, with respect to the starting compound of formula (II).

The compound of formula (IV) which is produced during the reaction of the present invention is a novel compound which has not been disclosed in any of the prior publication. If necessary, the compound of formula (IV) can be isolated and then reacted under the same condition as above to prepare the desired compound of formula (I).

Accordingly, the present invention also provides a novel ethylidene dithiocarbazate compound represented by the following formula (IV). The present invention further includes a process for preparation of the compound of formula (I) characterized in that the compound of formula (IV) is cyclized in the presence of a base as depicted in the following reaction scheme (2):

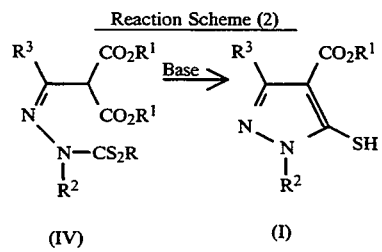

In the above reaction scheme R, $R^1$, $R^2$ and $R^3$ are defined as above.

The reaction according to the reaction scheme (2) is effectively conducted under the same condition as the reaction according to the above reaction scheme (1) and is characterized by a high purity of about 99% of the desired compound prepared in this reaction.

According to the processes of the present invention as specifically described, the desired compound of formula (I) can be very simply and efficiently synthesized in the one-step procedure in any case; it is not possible to produce the regioisomeric compound as being produced in the prior known method; the reaction can be completed in a short time under the considerably mild reaction condition; and the desired compound can be obtained in a high purity and a high yield.

Both the compound of formula (II) and the compound of formula (III), which are used as starting materials in the present invention, are the known compounds and can be readily obtained as a commercial product. However, particularly in the case of the starting compound of formula (II) it is more economical to synthesize the compound (II) for use in the reaction of the present invention.

However, when the compound of formula (II) is prepared according to the known method, there is a problem related to the reaction selectivity in many cases. For example, the compound of formula (II) can be prepared by reacting a monoalkyl hydrazine with potassium hydroxide and carbon disulfide ($CS_2$) in a polar solvent such as alcohols and then subjecting to the esterification with methyl iodide or according to the method described in U.S. patent specification No. 4,064,262, Japanese Laid-open Patent Publication No. (sho) 61-109771, etc. However, according to such known methods, since the reaction selectivity in the esterification step is low, there is the problem in that the by-product of formula (II'') may be produced and therefore the yield of the desired compound of formula (I) is lowered to 60 to 85%:

(II'')

wherein R is defined as above.

Thus, the present inventors have repeatedly studied to solve the problems involved in the prior methods and found that by carrying out the esterification step in the manner of a two-phase reaction comprising a non-polar solvent and a phase-transfer catalyst the reaction selectivity can be significantly improved and the desired compound of formula (IV) can be produced in a high purity and a high yield.

Therefore, the other object of the present invention is to provide a novel process for preparation of the compound of formula (II) to be used as the starting compound in the present invention, according to the following reaction scheme (3):

Reaction Scheme (3)

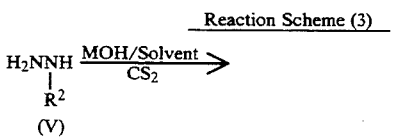

-continued
Reaction Scheme (3)

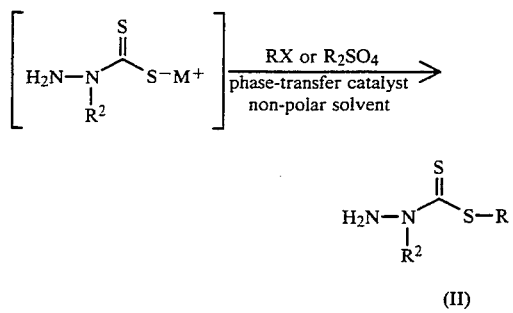

In the above reaction scheme, R and $R^2$ are defined as above, X represents a halogen and M represents an alkali metal.

The above method is specifically explained hereinafter.

First, the base is completely dissolved in a solvent and then carbon disulfide is added thereto in one portion and alkyl hydrazine (V) is slowly added dropwise, and the mixture is thoroughly stirred until the reaction is no longer progressed. As a base for this procedure, a metal hydroxide is used and particularly sodium hydroxide or potassium hydroxide is preferable. Each of carbon disulfide and the base is used in an amount of 1.0 to 1.5 equivalent weight and preferably 1.01 to 1.05 equivalent weight, with respect to the compound of formula (V). Although the base which can be used in this reaction includes water or alcohols, it is advantageous that the use of water in an amount of 4.0 equivalent weights or more can generally induce a uniform reaction. The reaction temperature is maintained conventionally in the range of 0° to 40° C. and preferably in the range of 0° to 15° C. to prevent the loss of the reactants. Particularly, it is preferable to reduce the internal temperature of a reaction vessel to 0° to 5° C. prior to the addition of carbon disulfide. The alkyl compound (V) is slowly added in a manner such that the internal temperature of reaction vessel does not exceed 15° C.

Subsequently, to the reaction mixture containing a carbazic acid derivative thus produced are added a non-polar organic solvent and a phase-transfer catalyst and then an electrophilic sustance suitable for the desired compound is added thereto to practice the esterification reaction.

As the non-polar organic solvent which can be used in this reaction, an aprotic solvent, for example, methylene dichloride, ethylene dichloride, n-hexane, n-heptane or toluene is preferable. The non-polar organic solvent is used in a solvent amount which is generally used in this type of reaction, for example, in an amount of 5 to 40 equivalent weights.

In this reaction, the phase-transfer catalyst may be quaternary ammonium halide or tertiary amine, with quaternary ammonium halide, particularly tetrabutyl ammonium bromide, being preferable. The used amount of the catalyst is 0.001 to 1.0 equivalent weight, preferably 0.01 to 0.1 equivalent weight.

The electrophilic substance which can be used in this reaction includes an alkyl sulfate ($R_2SO_3$) or an alkyl halide (R-X) and is used in an amount of 1.0 to 2.0 equivalent weights, preferably 1.0 to 1.05 equivalent weights. In this reaction, the electrophile is preferably added at a uniform rate over 2 to 3 hours. Herein, although the term "alkyl" should be understood to include all the definitions for the substituent R in the desired compound, the preferred electrophile is a sulfate compound having methyl, ethyl, propyl, isopropyl, allyl, butyl, benzyl or p-nitrobenayl group, or a chloride or bromide compound, with dimethyl sulfate, allyl bromide or benzyl chloride being most preferable. Although the esterification reaction can be practiced at the temperature of 0° C. to the refluxing temperature of the solvent used therein, the reaction temperature in the range of 0° C. to 25° C. can minimize the production of by-products and provide the best result.

The method of the present invention as described above provides many advantages in the industrial aspect since the desired compound (II) having a purity of 95% or more can be obtained in a high yield of 99% or more according to the present method.

All the reaction procedures according to the present invention as described above can be represented by the following reaction scheme (4):

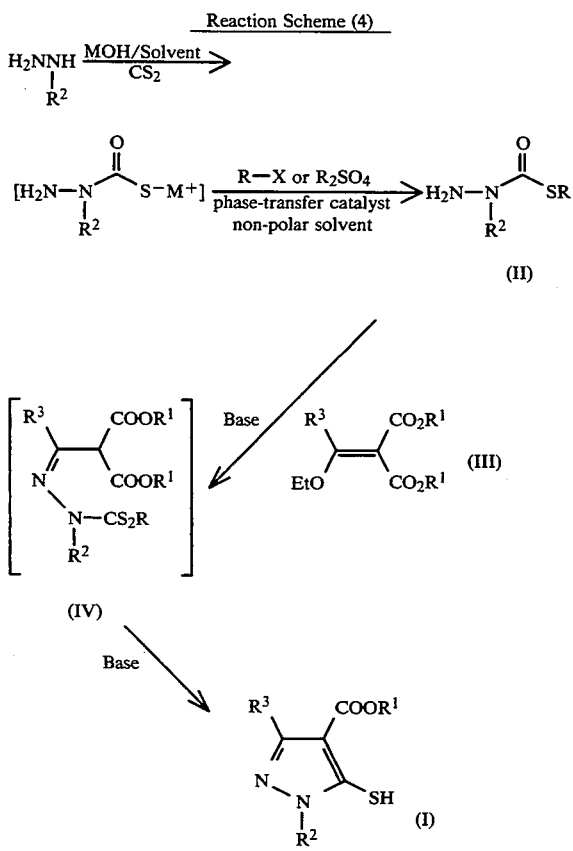

In the above reaction scheme R, $R^1$, $R^2$, $R^3$, M and X are defined as above.

The present invention will be more specifically illustrated by the following examples. However, it should be understood that the present invention is not limited by these examples in any manner. In these examples, the purity of the resulting product was analyzed by a gas chromatography.

EXAMPLE 1

Synthesis of 2-methyldithiocarbazic acid methyl ester

420mg (10.5 mM) of sodium hydroxide was completely dissolved in-5.0 g of water and then the resulting solution was cooled down to maintain at 0° to 5° C. At this temperature 799 mg (10.5mM) of carbon disulfide was; added thereto in one portion and then 461 mg (10.0 mM) of methyl hydrazine was slowly added over 30 minutes during which the internal temperature should be maintained below 10° C. While maintaining the temperature of about 10° C., the stirring was continued for 3 hours and then 10.0 g of methylene dichloride and 42 mg(0.15 mM) of n-butylammonium bromide were added to this reaction mixture. 1274 mg (10.1 mM) of dimethyl sulfate was slowly added thereto over 30 minutes and then allowed to further react for one hour. The organic layer was separated, dried over anhydrous magnesium sulfate, filtered and then distilled to remove the solvent to obtain 1294 mg (Yield 95%) of the title compound which was identified to have a purity of 98% by gas chromatography.

EXAMPLE 2

Synthesis of 2-methyldithiocarbazic acid allyl ester

According to the same procedure as EXAMPLE 1 except that as the electrophile 1222 mg (10.1 mM) of allyl bromide is used instead of dimethyl sulfate, 1558 mg (Yield 96%) of the title compound was obtained. The purity of the resulting product was identified as 97% by gas chromatography.

EXAMPLE 3

Synthesis of 2-methyldithiocarbazic acid benzyl ester

The reaction was carried out according to the same procedure as EXAMPLE 1 except that as an esterifying solvent 30.0 g of n-hexane is used instead of methylene dichloride and as the electrophile 1279 mg(10.0 mM) of benzyl bromide is used instead of dimethyl sulfate, and then the resulting product was extracted with methylene chloride, dried with anhydrous magnesium sulfate and filtered to obtain 2102 mg (Yield 99%) of the title compound. The purity of the resulting compound was identified as 95% by gas chromatography.

EXAMPLE 4

Synthesis of 2-methyldithiocarbazic acid ethyl ester

According to the same procedure as EXAMPLE 1 or 3 except that as the electrophile 1555 mg (10.1 mM) of diethyl sulfate is used, 1425 mg (Yield 95%, Purity 96%) of the title compound was obtained.

EXAMPLE 5

Synthesis of 2-methyldithiocarbazic acid propyl ester

According to the same procedure as EXAMPLE 1 or 3 except that as the electrophile 1838 mg (10.0 mM) of dipropyl sulfate is used, 1591 mg (Yield 97%, Purity 95%) of the title compound was obtained.

EXAMPLE 6

Synthesis of 2-methyldithiocarbazic acid isopropyl ester

According to the same procedure as EXAMPLE 1 or 3 except that as the electrophile 793 mg (10.1 mM) of isopropyl chloride is used, 1542 mg (Yield 94%, Purity 96%) of the title compound was obtained.

EXAMPLE 7

Synthesis of 2-methyldithiocarbazic acid butyl ester

According to the same procedure as EXAMPLE 1 or 3 except that as the electrophile 944 mg(10.1 mM) of butyl chloride is used, 1718 mg (Yield 96% Purity 95%) of the title compound was obtained.

EXAMPLE 8

Synthesis of 2-methyldithiocarbazic acid t-butyl ester

According to the same procedure as EXAMPLE 1 or 3 except that as the electrophile 944 mg(10.1 mM) of t-butyl chloride is used, 1754 mg (Yield 98%, Purity 93%) of the title compound was obtained.

EXAMPLE 9

Synthesis of 2-methyldithiocarbazic acid p-nitrobenzyl ester

According to the same procedure as EXAMPLE 1 or 3 except that as the electrophile 1732 mg (10.1 mM) of p-nitrobenzyl chloride is used, 2442 mg (Yield 95%, Purity 96%) of the title compound was obtained.

EXAMPLE 10-13

Synthesis of benzyl 3-[2',2'-(diethoxycarbonyl)ethylidene]-2-methyldithiocarbazate In EXAMPLES 10 to 13, the title compound was prepared according to the procedures as described below, using the solvent, base and reaction conditions as listed in the following Table 1.

Under nitrogen atmosphere, 882 mg (4.08 mM) of diethylethoxymethylene malonate and 849 mg (4.00 mM) of benzyl 2-methyldithiocarbazate were introduced into 10ml of the solvent and then heated to 40° C. to produce a homogeneous solution. To this reaction mixture was added the base over about 10 minutes and then the reaction was conducted under the reaction condition described in Table 1. The completion of the reaction was identified with TLC (Rf: 0.35, developer: n-hexane/ethyl acetate=4/1) and then water was added to the reaction mixture. The reaction solution was extracted with methylene dichloride to separate the organic layer which was then dried over magnesium sulfate and distilled to remove the solvent to obtain the title compound in a liquid state as described in the following Table 1. The resulting product was identified as having the following physical properties.

$^1$H NMR (270 MHz, CDCl$_3$/TMS): δ1.245–1.385 (m, 6H), 3.766(s,3H), 4.151–4.304(m,4H), 4.408(s,2H), 7.272–7.360(m,5H0, 7.884(d,1H,J=11.1 Hz), 10.404(d,1H,J=11.1 Hz)

MS (70 eV): m/z 382(M+), 336, 290, 259, 223

40° C. to produce a homogeneous solution. To this reaction mixture was added 327 mg (4.80 mM) of sodium ethoxide. Then the reaction was conducted at 40° C. for one hour and water was added to the reaction mixture. The reaction mixture was extracted with methylene dichloride to separate the organic layer which was dried over magnesium sulfate, filtered and then distilled to completely remove the solvent to obtain 1213 mg (Yield 99%, Purity 98%) as having the following physico-chemical properties.

$^1$H NMR (270 MHz, CDCl$_3$/TMS): 1.306(t,3H,J=7.3 Hz), 1.365(t,3H, J=6.5 Hz), 2.557 (s,3H) , 3.775(s,3H), 4.216(q,2H,J=7.3 Hz) 4.299(q,2H,J=6.5 Hz) , 7.898(d,1H,J=11.0 Hz), 10.424 (d,1H, J=11.0 Hz)

MS (70 eV):m/z 306(M+), 259, 204, 187

EXAMPLE 15

Synthesis of allyl 3-[2',2'-(diethoxycarbonyl)ethylidene]-2-methyldithiocarbazate Under nitrogen atmosphere, 882 mg (4.08 mM) of diethylethoxymethylene malonate and 649 mg (4.00 mM) of allyl 2-methyldithiocarbazate were introduced into 10 ml of absolute ethanol and then heated to 40° C. to produce a homogeneous solution. To this reaction mixture was added 327 mg (4.80 mM) of sodium ethoxide. Then the reaction was conducted at 40° C. for 30 minutes and water was added to the reaction mixture. The reaction mixture was extracted with methylene dichloride to separate the organic layer which was dried over magnesium sulfate, filtered and then distilled to completely remove the solvent to obtain 1263 mg (Yield 95%, Purity 98%) as having the following physico-chemical properties.

$^1$H NMR (270 MHz, CDCl$_3$/TMS): δ1.256–1.387(m,6H) , 3.76(s,3H) , 3.858(d,2H,J=6.8 Hz) 4.175–4.335(m,4H) , 5.153–5.336(m, 2H), 5.824–5.924(m, 1H), 7.887(d,1H,J=11.1 Hz), 10.415(d, 1H,J=11.1 Hz)

MS (70 eV): m/z 332(M+), 287, 245, 217

EXAMPLE 16

Synthesis of 4-ethoxycarbonyl-1-methyl-5-pyrazolemercaptan from methyl 2-methyldithiocarbazate compound 882 mg of diethylethoxymethylene malonate and 545 mg of methyl 2-methyldithiocarbazate in 10 ml of abso-

TABLE 1

| Example No. | Solvent | Base[1] (eq. wt) | Reaction Temp.(°C.) | Reaction Time(hr) | Yield(%) | Purity[2](%) |
|---|---|---|---|---|---|---|
| 10 | EtOH | NaOEt(1.05) | 40 | 1.5 | 99 | 98 |
| 11 | EtOH | NaOEt(2.0) | 40 | 0.5 | 98 | 97 |
| 12 | THF | KOEt(1.10) | 0 | 0.5 | 98 | 96 |
| 13 | MDC | Et$_3$N(2.0) | Reflux | 72 | 85 | 80 |

Note:
[1]The equivalent weight of base is based on the dithiocarbazate of formula (II).
[2]Purity is represented by GC area %.

EXAMPLE 14

Synthesis of methyl 3-[2',2'-(diethoxycarbonyl)ethylidene]-2-methyldithiocarbazate Under nitrogen atmosphere, 882 mg (4.08 mM) of diethylethoxy-methylene malonate and 545 mg (4.00 mM) of methyl 2-methyldithiocarbazate were introduced into 10 ml of absolute ethanol and then heated to lute ethanol were heated under nitrogen atmosphere to produce a homogeneous solution of the reaction mixture. To this solution was added sodium ethoxide, which was prepared by reacting 110 mg of sodium metal with 5 ml of absolute ethanol, over 10 minutes at room temperature and then the reaction mixture was heated under reflux for about 10 hours. After the completion of the reaction was identified by TLC or GC, 10 ml of water and 25 ml of methylene dichloride were added to the reaction mixture. The whole mixture was adjusted to pH 8 with 20% sulfuric acid to separate the layers. The aqueous layer was separated and adjusted to pH 2. The resulting product was extracted with 25 ml of methylene dichloride. The extract was evaporated to remove the solvent and then distilled in vacuo (b.p. 107° C., 0.1 torr) to obtain 707 mg (Yield 95%, Purity 95%) of the title compound.

EXAMPLE 17

Synthesis of 4-ethoxycarbonyl-1-methyl-5-pyrazolemercaptan from allyl 2-methyldithiocarbazate 882 mg of diethylethoxymethylene malonate and 649 mg of allyl 2-methyldithiocarbazate in 10 ml of absolute ethanol were heated under nitrogen atmosphere to produce a homogeneous solution of the reaction mixture. To this solution was added sodium ethoxide, which was prepared by reacting 110 mg of sodium metal with 5 ml of absolute ethanol, over 10 minutes at room temperature and then the reaction mixture was heated under reflux for about 10 hours. After the completion of the reaction was identified by TLC or GC, the reaction mixture was distilled to remove ethanol. Working-up was carried out according to the same procedure as EXAMPLE 16 to obtain 700 mg (Yield 94%, Purity 96%) of the title compound.

EXAMPLE 18

Synthesis of 4-ethoxycarbonyl-1-methyl-5-pyrazolemercaptan from benzyl 2-methyldithiocarbazate 882 mg of diethylethoxymethylene malonate and 545 mg of benzyl 2-methyldithiocarbazate in 10 ml of absolute ethanol were heated under nitrogen atmosphere to produce a homogeneous solution of the reaction mixture. To this solution was added sodium ethoxide, which was prepared by reacting 110 mg of sodium metal with 5 ml of absolute ethanol, over 10 minutes at room temperature and then the reaction mixture was heated under reflux for about 10 hours. After the completion of the reaction was identified by TLC or GC, the reaction mixture was distilled to remove ethanol. Working-up was carried out according to the same procedure as EXAMPLE 16 to obtain 685 mg (Yield 92%, Purity 97%) of the title compound.

EXAMPLE 19

Synthesis of 4-ethoxycarbonyl-1-methyl-5-pyrazolemercaptan from methyl dithiocarbazate compound 1226 mg of methyl 3-[2',2'-(diethoxycarbonyl)ethylidene]-2-methyldithiocarbazate and 327 mg of sodium ethoxide were added to 10 ml of absolute ethanol and the mixture was heated to reflux under nitrogen atmosphere for about 10 hours. After the completion of the reaction was identified by TLC or GC, the reaction mixture was distilled to remove ethanol. To the residue were added 10 ml of water and 25 ml of methylene dichloride. The resulting mixture was adjusted to pH 8 with 20% sulfuric acid to separate the layers. The aqueous layer was separated and adjusted to pH 2. The resulting product was extracted with 25 ml of methylene dichloride. The extract was distilled in vacuo (b.p. 107° C., 0.1 torr) to obtain 708 mg (Yield 95%, Purity 99%) of the title compound.

$^1$H NMR(CDCl$_3$): δ7.87(s,1H), 6.45(s,1H), 4.31(q,2H), 3.78(s,3H), 1.36 (t,3H)

EXAMPLE 20

Synthesis of 4-ethoxycarbonyl-1-methyl-5-pyrazolemercaptan using sodium hydroxide base According to the same procedure as EXAMPLE 19 except that 176 mg of sodium hydroxide as a base was added and then allowed to react for 10 hours, 700 mg (Yield 94%, Purity 98%) of the title compound was obtained.

EXAMPLE 21

Synthesis of 4-ethoxycarbonyl-1-methyl-5-pyrazolemercaptan from allyl dithiocarbazate compound According to the same procedure as EXAMPLE 19 except that 1330 mg of allyl 3-[2',2'-(diethoxycarbonyl)ethylidene]-2-methyldithiocarbazate prepared in EXAMPLE 15 was used, 723 mg (Yield 97%, Purity 99%) of the title compound was obtained.

EXAMPLE 22

Synthesis of 4-ethoxycarbonyl-1-methyl-5-pyrazolemercaptan from benzyl dithiocarbazate compound According to the same procedure as EXAMPLE 19 except that 1532 mg of benzyl 3-[2',2'-(diethoxycarbonyl)ethylidene]-2-methyldithiocarbazate prepared in EXAMPLE 10-13, 730 mg (Yield 98%, Purity 98%) of the title compound was obtained.

Although this invention has been described in its preferred form with a certain degree of particularity, it is appreciated by those skilled in the art that the present disclosure of the preferred form has been made only by way of example and that numerous changes in the details of the construction, combination and rearrangement of parts may be resorted to without departing from the spirit and scope of the invention.

What is claimed is:

1. A process for preparation of 5-pyrazolemercaptan derivatives represented by the following general formula(I),

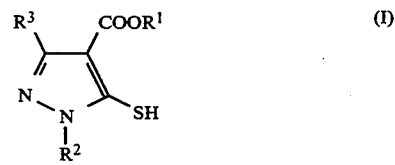

wherein $R^1$ represents hydrogen, $C_1$–$C_4$ alkyl, allyl or propargyl, $R^2$ represents hydrogen, $C_1$–$C_4$ alkyl, or a phenyl group which can contain one or more substituent selected from the group consisting of halogen, nitro and methyl at an optional position, and $R^3$ represents hydrogen, methyl, ethyl or phenyl, characterized in that an ethylidene dithiocarbazate compound of the following formula (IV) ,

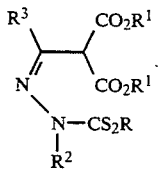

wherein R represents $C_1$–$C_4$ alkyl, $C_2$–$C_4$ alkenyl, aralkyl or aryl, and $R^1$, $R^2$ and $R^3$ are defined as above, is reacted with a base.

2. The process of claim 1, characterized in that R represents methyl, ethyl, propyl, isopropyl, n-butyl, t-butyl, allyl, benzyl or p-nitrobenzyl; $R^1$ represents methyl or ethyl; $R^2$ represents methyl; and $R^3$ represents a hydrogen atom.

3. The process of claim 1, characterized in that said base is sodium ethoxide, sodium hydroxide or potassium hydroxide and is used in an amount of 1.0 to 5.0 equivalent weight with respect to the compound of formula(IV).

4. The process of any one of claims 1 to 3, characterized in that the reaction is carried out in ethanol solvent.

* * * * *